United States Patent [19]

Smith, Jr.

[11] Patent Number: 5,196,138
[45] Date of Patent: Mar. 23, 1993

[54] PREPARATION OF MIXED LITHIUM AMIDE REAGENTS

[75] Inventor: W. Novis Smith, Jr., Philadelphia, Pa.

[73] Assignee: Cyprus Foote Mineral Company, Malvern, Pa.

[21] Appl. No.: 419,966

[22] Filed: Oct. 11, 1989

Related U.S. Application Data

[63] Continuation-in-part of Ser. No. 374,740, Jun. 30, 1989.

[51] Int. Cl.$^5$ ................................................ C09K 3/00
[52] U.S. Cl. ................................................ 252/182.12
[58] Field of Search ................................... 252/182.12

[56] References Cited

U.S. PATENT DOCUMENTS

| | | |
|---|---|---|
| 3,542,512 | 11/1970 | Honeycutt . |
| 4,595,779 | 6/1986 | Morrison et al. . |
| 4,622,410 | 11/1986 | Hamanaka et al. .............. 549/304 |
| 4,629,581 | 12/1986 | Boller et al. ................. 252/299.63 |
| 4,693,841 | 9/1987 | Hittich et al. ................. 252/299.62 |
| 4,827,007 | 5/1989 | Choi ................................ 556/444 |
| 4,944,894 | 7/1990 | Mehta et al. .................. 252/182.12 |
| 5,011,947 | 4/1991 | Catt et al. ........................ 549/292 |

OTHER PUBLICATIONS

Schlosser et al., Chem. Ber., 102, 1944–1953 (1969).
Normant et al., Chem. Abs., 70, abs. #105864h (1969).
Stowell, Carbanions in Organic Synthesis, pp. 14–15, John Wiley & Sons (1979).
Lochmann et al., J. Organometallic Chem., 179, 123–132 (1979).
"Lithium Diisopropylamide" Litcho Corp. pp. 1–4.

Primary Examiner—Edward A. Miller
Attorney, Agent, or Firm—John Lezdey

[57] ABSTRACT

A method for preparing a poorly soluble lithium amides in greater concentration by preparing a mixture of lithium amides wherein one of said lithium amides is soluble and another lithium amide is less soluble, and the reagent compositions formed thereby.

16 Claims, No Drawings

PREPARATION OF MIXED LITHIUM AMIDE REAGENTS

RELATED APPLICATION

This application is a continuation-in-part of application Ser. No. 374,740 filed Jun. 30, 1989 of W. Novis Smith entitled, "Stable Lithium Amides and Reagent Compositions Thereof".

FIELD OF THE INVENTION

The present invention relates to a process for improving the solubility of ordinarily poorly soluble lithium amides and to reagent compositions having greater concentrations of the poorly soluble lithium amides in a non-reactive hydrocarbon solvent. More particularly, the present invention provides a means for preparing a reagent composition with a higher concentration of an ordinarily poorly soluble or alternatively a less soluble lithium amide through the preparation of mixed lithium amides. There is also provided a improvement in low temperature solubility. Additionally, the lithium amides can be tailored for selective reactions.

BACKGROUND OF THE INVENTION

Lithium amides, for example, lithium diisopropylamide, are widely used as a reagents in the preparation of pharmaceuticals and specialty chemicals. Lithium amides are particularly useful for the preparation of lithium acetylide compounds which are used to form acetylenic substituted organic compounds such as in steroid and fragrance intermediates. Also, they can be used to form other lithium acetylides such as propynyl lithium, cyclopentadienyl lithium, and the like. In order to form the lithium acetylide, acetylene is reacted with a lithium amide, such as lithium diisopropylamide, just prior to reacting the newly formed lithium acetylide with the ketone or other reagent in the same reactor. All of these steps are performed below 0° C. It is preferable to use solutions of the lithium amides in inert solvents such as heptane, cycloheptane or toluene. Usually, it is necessary to add an ether cosolvent such as tetrahydrofuran at this point to increase the limited solubility of the reagents and the subsequently formed lithium salt of the product from the reaction with the ketone. The lithium amide may be added as a preformed solution or it may be formed in the same reactor by reacting an alkyllithium, such as n-butyllithium, with an amine, such as diisopropyl amine. In either case, the lithium amide usually exhibits lower solubility than desired for maximum reactivity and yet there is a need to minimize the amount of solvents employed.

In order to increase the concentration of the lithium amide in the preformed solutions, ethers such as tetrahydrofuran and/or complexing agents such as organomagnesium compounds have been added to increase the solubility of the lithium amide in solution. The presence of the ethers makes these solutions unstable and they decompose on standing in storage at room temperature. The presence of magnesium compounds in the reaction and subsequent workup is undesirable because the possibility of lower reactivity and lower yields of desired products plus the more difficult workup due to the presence of the formed magnesium oxide which is highly insoluble and is formed during washing.

Additionally, when tetrahydrofuran is used as the solvent, it has been found necessary to limit the amount of tetrahydrofuran to no more than one mole for each mole of lithium amide in order to minimize degradation of the system. Also, it is known that reaction of n-butyl lithium in all ethers, especially tetrahydrofuran and ethylene glycol dimethyl ether, results in rapid cleavage of the ethers at room temperature.

Mixtures of lithium diisopropyl amide and magnesium bis(diisopropyl)amide are known in a solvent of tetrahydrofuran and n-heptane. The magnesium bis(-diisopropyl)amide is used to improve thermal stability and low temperature solubility.

It is preferable to use only active reagents to obtain the synergistic solubility effects of one lithium amide in the presence of another so as to obtain practical concentrations of lithium amide solutions.

The use of ethers or complexing reagents containing magnesium, aluminum, or the like results in impurities and by products which require further processing in order to remove. These impurities and by-products may cause side reactions which lower the yield.

It is also commercially desirable to be able to ship solutions that are about 2 Molar in order to minimize the amount of solvent required both from a transportation point of view and to permit a more concentrated reaction to be run when adding a preferred lithium amide in solution.

The article of Keith Smith entitled "Lithiation and Organic Synthesis", *Chemistry In Britain*, January 1982, pages 29-32, discloses the preparation of lithium dialkyl amides for use as lithiating agents by the reaction of organolithium reagents in aliphatic hydrocarbon solvents.

U.S. Pat. No. 3,542,512 to Honeycutt relates to the preparation of lithium amide by contacting lithium metal with liquid ammonia and then heating the mixture at a temperature above 150 degrees C in an inert liquid medium. The inert liquid medium includes aromatic compounds having a boiling point above 200 degrees C.

It is an object of the present invention to provide a lithium amide reagent composition having greater amounts of an ordinarily poorly soluble lithium amide in solution.

It is a further object of the invention to provide a process for preparing ordinarily poorly soluble lithium amides in higher concentrations in solution and in various solvents.

It is a still further object of the invention to prepare lithium amides which are to be used in selective reactions by admixing at least two different lithium amides with different reaction activities and achieve an overall reactivity which is an improvement over the sum of the two independents.

It is a yet further object of the invention to solubilize lithium amides which are considered insoluble at the time of preparation.

It is a yet still further object of the invention to prepare ordinarily poorly soluble lithium amides in situ and to utilize the resulting mixture to carry on further reactions.

It is understood that the term "poorly soluble" as used herein refers to a solubility of 0.45M or less in heptane or hydrocarbon solvents.

SUMMARY OF THE INVENTION

In accordance with the present invention, it has been found that ordinarily poorly soluble lithium amides could be prepared so as to form reagent compositions of the mixed amides with greater molar amounts of the amides in solution. Moreover, the resulting improved lithium amide reagent compositions can be formed with a wide variety of solvents.

The invention provides the preparation of lithium amides by the step of reacting in a suitable solvent an alkyl lithium and a mixture of amines of the formula selected from the group consisting of:

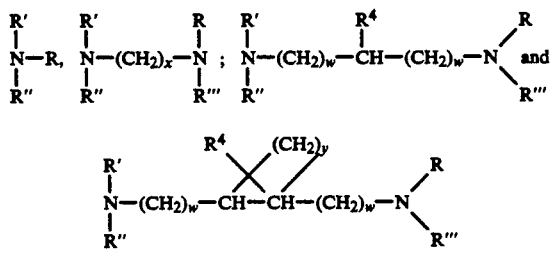

wherein at least one lithium amide formed is by itself soluble in said solvent and one of said lithium amides is by itself poorly soluble or alternatively less soluble in said solvent, and R is a hydrogen, an alkyl of 1 to 8 carbon atoms, alkyl phenyl or an alkyl monocyclic aliphatic group, R' and R" are the same or different and each represent hydrogen, an alkyl of 1 to 8 carbon atoms or an alkyl monocyclic aliphatic group, R''' is hydrogen, alkyl or alkoxy, $R^4$ is hydrogen, alkyl or phenyl; W is from 0 to 4, x is an integer of 2 to 8, and y is an integer of 2 to 6, with the proviso that at least one of R, R', R" and R''' is hydrogen.

The solvent which may be used in connection with the present invention alone or in admixture include hydrocarbons such as cycloalkanes, more particularly cyclopentane, cyclohexane, cycloheptane, and the like, aliphatic hydrocarbons such as heptane, hexane, and the like, benzene, toluene, ethyl benzene, cumene, xylene, and the like.

Ethers may be utilized, such as tetrahydrofuran, but the invention provides the advantage that ethers need not be utilized. The amines which may be utilized in the preparation of the lithium amides of the invention include the alkyl amines such as methyl amine, isopropyl amine, isoamyl amine and the like, dialkyl amines such as dimethyl amine, diethyl amine, diisopropyl amine, diisobutyl amine, diisoamyl amine, dialkylheptyl amine, di(alkylhexyl) amine, for example, di(methylhexyl) amine and di(ethyl hexyl) amine, N, N'-dialkyl alkylene diamine, for example, N, N'-di(tert-butyl)ethylene diamine, N, N-dimethylaminoethyl amine, N, N-dimethylaminopropyl amine, N, N, N'-trimethylethylene diamine, N, N-dipropylaminopropylene amine, N, N'-diethyl -1, 3-propane diamine, N, N¹-diethyl-1,2-propane diamine, N, N, N'-trimethylethylene diamine, N, N, N'-triethylethylene diamine, N, N-dimethyl-N'-ethylethylene diamine, and the like.

The preferred amines which may be utilized in the invention include butyl amine, diisoamyl amine, diisobutyl amine, di-sec-butylamine, diisopropyl amine, dimethylaminopropyl amine (DMAPA) and di(ethylhexyl) amine.

It has been surprisingly discovered that the preparation of a mixture of lithium amides increases the solubility of the ordinarily poorly soluble lithium amides in the solvents. It is believed that the increased solubility occurs because the presence of the soluble amide breaks up the crystallinity of the poorly soluble amide. Therefore the crystalline growth of the lithium amides is retarded or made difficult so that it does not crystallize readily. The process of the invention is especially suited for reactions and solutions containing branch chained dialkyl amines.

The mixed lithium amides solutions make it possible to tailor the selectively or reactivity of the lithium amide toward metallations and other reactions. This can be accomplished for example by using a mixture of a lithium amide of a sterically bulky amine with that of a less bulky one to achieve reactivity that is intermediate between the two amides. In another situation, a mixture of a dialkyl amine and a N, N, N'-trialkyl diamine or even a N, N-dialkyl diamine can be used to obtain the optimum reactivity characteristics of each type of amide.

The following table illustrates the solubility of various lithium amides in toluene, cyclohexane and heptane:

TABLE 1

| Starting Amine 1 | Mole % | Starting Amine 2 | Mole % | Solvent | Molar Conc |
|---|---|---|---|---|---|
| Diisopropyl amine | 100 | — | | heptane | 0.42 |
| Diisopropyl amine | 100 | — | | toluene | 0.49 |
| Diisobutyl amine | 100 | — | | heptane | 1.08 |
| Diisobutyl amine | 100 | — | | toluene | 2.1 |
| Diisobutyl amine | 100 | — | | cyclohexane | >1.3 |
| Diethyl amine | 100 | — | | heptane | 0.04 |
| Diethyl amine | 100 | — | | toluene | 0.05 |
| Di-sec-butyl amine | 100 | — | | heptane | >1.3 |
| Di-sec-butyl amine | 100 | — | | toluene | >2.2 |
| Di-sec-butyl amine | 100 | — | | cyclohexane | >1.3 |
| Dimethyl-aminopropyl amine (DMAPA) | 100 | — | | toluene | >2.2 |
| Dimethyl-aminopropyl amine (DMAPA) | 100 | — | | cyclohexane | 0.79 |
| Diethylaminoethylamine | 100 | — | | toluene | >2.2 |
| N,N,N'-Tri-methylethylene diamine | 100 | — | | toluene | >2.2 |
| N,N,N'-Tri-methylethylene diamine | 100 | — | | toluene | >2.2 |
| N,N,N'-Tri-methyl-1,3-propylene diamine | 100 | — | | toluene | >2.2 |
| Cyclohexyl amine | 100 | — | | toluene | >0.3 |

In accordance with another embodiment of the invention, there is prepared a reagent composition comprising a solvent selected from the group consisting of a monocyclic aromatic solvent, an inert hydrocarbon solvent and mixtures thereof, and a mixture of at least two lithium amides selected from the group consisting:

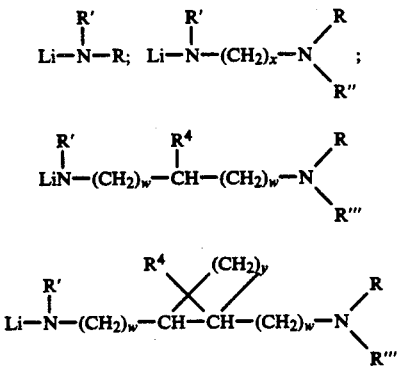

wherein at least one of said lithium amides is by itself soluble in said solvent and one of said lithium amides is by itself poorly soluble or alternatively less in said solvent, and R is a hydrogen, an alkyl of 1 to 8 carbon atoms, alkyl phenyl or an alkyl monocyclic aliphatic group, R' and R" are the same or different and each represent hydrogen, an alkyl of 1 to 8 carbon atoms, alkyl phenyl or an alkyl monocyclic aliphatic group, R''' is hydrogen, alkyl or alkoxy, $R^4$ is hydrogen, alkyl or phenyl, W is from 0 to 4, x is an integer of 2 to 8, and y is an integer of 2 to 6.

Advantageously, the composition comprises at least a 1.0 molar solution of the lithium amide solution.

The invention provides an additional advantage when the composition is a mixture of lithium amides wherein both amides are soluble but the mixture has selective reactivity because of the dissimilar structure of the amides involved.

The following examples are illustrative of the practice of the method of the present invention. It will be understood, however, that is not to be construed as in any way limitative of the full scope of the invention since various changes can be made, without departing from the spirit of the teachings contained herein, in the light of the guiding principles which have been set forth above. All percentages herein stated are based on weight except wherein noted.

EXAMPLE 1

Preparation of Mixed Lithium Amides

To 20 ml. of 15% of 2M n-butyl lithium (0.04 mole) in toluene is added 3.8 ml. of diisobutyl amine and 2.8 ml. of diisopropyl amine. The mixture is stirred for 10 minutes. A 22% by weight reagent composition is formed containing a 50—50 mole % by weight of mixed lithium amides.

EXAMPLE 2

Solutions of mixed lithium amides were prepared by the addition of stoichiometric amounts of two or more amines to n-butyllithium in hydrocarbon solvents under an inert atmosphere. The combined moles of each amine was equivalent to the contained moles of alkyllithium (15% n-butyllithium in heptane and 24% in toluene were used for the examples below). The solution was stirred and maintained at room temperature during addition. The solution or slurry was allowed to stand for 48 hours. The solution was filtered, hydrolyzed and titrated for a total base to pH 7. The molarity of the soluble mixed lithium amide solution was calculated by dividing the total soluble base by two. In the mixtures where there was a poorly soluble lithium amide and a soluble lithium amide, the combined solubility of the lithium amides was more than expected from the separate solubility of each; The results were as follows:

| Amine 1 | % Mole | Solubilizing Amine | % Mole | Solvent | Solution Molarity |
|---|---|---|---|---|---|
| Diisopropyl Amine | 20 | Diisobutyl amine | 80 | heptane | 1.1 |
| Diisopropyl amine | 40 | Diisobutyl amine | 60 | heptane | 1.1 |
| Diisopropyl amine | 60 | Diisobutyl amine | 40 | heptane | 1.1 |
| Diisopropyl amine | 80 | Diisobutyl amine | 20 | heptane | 1.1 |
| Diisopropyl amine | 20 | Diisobutyl amine | 80 | toluene | >2.2 |
| Diisopropyl amine | 40 | Diisobutyl amine | 60 | toluene | >2.2 |
| Diisopropyl amine | 60 | Diisobutyl amine | 40 | toluene | >2.2 |
| Diisopropyl amine | 80 | Diisobutyl amine | 20 | toluene | >2.2 |
| Diisopropyl amine | 20 | Dimethylaminopropyl amine (DMADA) | 80 | heptane | 1.3 |
| Diisopropyl amine | 40 | Dimethylaminopropyl amine | 60 | heptane | 1.2 |
| Diisopropyl amine | 60 | Dimethylaminopropyl amine | 40 | heptane | 1.0 |
| Diisopropyl amine | 80 | Dimethylaminopropyl amine | 20 | heptane | 1.0 |
| Diisopropyl amine | 20 | Dimethylaminopropyl amine | 80 | toluene | >2.2 |
| Diisopropyl amine | 40 | Dimethylaminopropyl amine | 60 | toluene | >2.2 |
| Diisopropyl amine | 60 | Dimethylaminopropyl amine | 40 | toluene | >2.2 |
| Diisopropyl amine | 80 | Dimethylaminopropyl amine | 20 | toluene | >2.2 |

In the case of dimethylaminopropyl amine, the basicity of both nitrogens was included in the calculation.

EXAMPLE 3

Following the procedure of Example 2, the solubilities of the following mixed lithium amides in toluene and heptane were determined.

| Less Soluble Starting amine 1 | Mole % | Starting amine 2 | Mole % | Solvent | Molar Conc |
| --- | --- | --- | --- | --- | --- |
| Diisopropyl amine | 80 | Diisobutyl amine | 20 | heptane | 1.1 |
| Diisopropyl amine | 80 | Diisobutyl amine | 20 | toluene | >2.2 |
| Diisopropyl amine | 80 | DMAPA | 20 | heptane | 1.0 |
| Diisopropyl amine | 80 | DMAPA | 20 | toluene | >2.2 |
| Diisopropyl amine | 50 | Di-sec-butyl amine | 50 | toluene | 1.2 |
| Diethyl amine | 80 | Diisobutyl amine | 20 | heptane | 0.60 |
| Diethyl amine | 80 | Diisobutyl amine | 20 | toluene | 0.45 |
| Diethyl amine | 80 | DMAPA | 20 | toluene | >2.2 |
| Diethyl amine | 90 | DMAPA | 10 | toluene | 1.0 |
| Diethyl amine | 95 | DMAPA | 5 | toluene | 1.0 |
| Diethyl amine | 50 | Di-sec-butyl amine | 50 | toluene | 0.63 |

What is claimed is:

1. A method of preparing lithium amides in a greater concentration which comprises the step of reacting in a suitable substantially ether free hydrocarbon solvent an alkyl lithium and a mixture of amines of the formula selected from the group consisting of:

$$\underset{R''}{\overset{R'}{\underset{|}{N}}}-R, \quad \underset{R''}{\overset{R'}{\underset{|}{N}}}-(CH_2)_x-N\underset{R''}{\overset{R}{\diagdown}} \quad \underset{R''}{\overset{R'}{\underset{|}{N}}}-(CH_2)_w-CH-(CH_2)_{\overline{w}}N\underset{R'''}{\overset{R}{\diagdown}}$$

and $$\underset{R''}{\overset{R'}{\underset{|}{N}}}-(CH_2)_w-\overset{R^4}{\underset{|}{CH}}\overset{(CH_2)_y}{\diagup}\overset{|}{\underset{|}{CH}}-(CH_2)_{\overline{w}}\underset{R}{\overset{R'''}{\underset{|}{N}}}$$

wherein at least one lithium amide formed is by itself soluble in said solvent and one of said lithium amides is by itself less soluble in said solvent, and R is hydrogen, an alkyl to 1 to 8 carbon atoms, alkyl phenyl or an alkyl monocyclic aliphatic group, R' and R" are the same or different and each represent hydrogen, an alkyl of 1 to 8 carbon atoms, an alkyl phenyl, an alkyl monocyclic aliphatic group, R'" is hydrogen, alkyl or alkoxy, $R^4$ is hydrogen, alkyl or phenyl, W is from 0 to 4, x is an integer of 2 to 8, and y is an integer of 2 to 6, with the proviso that at least one of R', R", and R'" is hydrogen.

2. The process of claim 1 wherein one of said amines is selected from the group consistent of diethyl amine, diamyl amine, diisopropyl amine, diisobutyl amine, di-sec-butylamine, diisoamyl amine, di(ethylhexyl)amine, sec-butylamine, n-propylamine, isopropyl amine, cyclohexylamine, ethyl amine and isobutylamine.

3. The process of claim 1 wherein one of said amine is selected from the group consisting of N, N'-di(t-butyl) ethylene diamine, N, N'-diethyl-1, 3-propylene diamine and N, N'-dimethyl-N'-ethylethylene diamine.

4. The process of claim 1 wherein said amine is selected from the group consisting of N, N, N'-trimethyl-1, 3-propane diamine, N, N, N'-trimethylethylene diamine and N, N, N'-triethylethylene diamine.

5. The process of claim 1 wherein said amine is N, N-dialkylaminoalkyl amine.

6. The process of claim 1 wherein the lithium amides are relatively soluble in a hydrocarbon solvent.

7. A process of preparing a solution of lithium amides of at least 0.1 molar solution comprising reacting an alkyl lithium with a mixture of diisopropylamine and diisobutylamine in a suitable ether free solvent.

8. The process of claim 7 wherein said solvent is an aliphatic hydrocarbon.

9. The process of claim 7 wherein said solvent is selected from the group consisting of an aromatic solvent, a hydrocarbon solvent and mixtures thereof.

10. The process of claim 7 wherein said solvent is a cyclic aliphatic hydrocarbon.

11. The process of claim 7 wherein said n-alkyl lithium is n-butyl lithium.

12. A process for preparing a solution of lithium amides of at least 0.1 molar solution comprising reacting in a suitable substantially ether free hydrocarbon solvent an alkyl lithium with mixtures of a monoamine of the formula:

$$\underset{R''}{\overset{R'}{\underset{|}{N}}}-R$$

wherein R, and R" each represent hydrogen, an alkyl group of 1 to 8 carbon atoms, alkyl phenyl or an alkyl monocyclic aliphatic group, and a diamine of the formula:

$$\underset{R''}{\overset{R'}{\underset{|}{N}}}-(CH_2)_x-\underset{R''}{\overset{R}{\underset{|}{N}}}$$

wherein R,R' and R" are as hereinbefore described and x is an integer of 2 to 8, whereby at least one lithium amide formed is by itself soluble in said solvent and one of said lithium amides is by itself less soluble in said solvent.

13. The process of claim 12 wherein the concentration of said lithium amides is at least 1.5 molar.

14. The process of claim 12 wherein said solvent is a monocyclic aromatic solvent.

15. The process of claim 14 wherein said solvent is selected from the group consisting of benzene, toluene and xylene.

16. The process of claim 12 wherein one of said lithium amides is lithium diisobutyl amide.

* * * * *